(12) United States Patent
Mekkaoui

(10) Patent No.: US 9,678,189 B2
(45) Date of Patent: Jun. 13, 2017

(54) MAPPING CARDIAC TISSUE ARCHITECTURE SYSTEMS AND METHODS

(71) Applicant: Choukri Mekkaoui, Boston, MA (US)

(72) Inventor: Choukri Mekkaoui, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/781,637

(22) PCT Filed: Apr. 3, 2014

(86) PCT No.: PCT/US2014/032766
§ 371 (c)(1),
(2) Date: Oct. 1, 2015

(87) PCT Pub. No.: WO2014/165646
PCT Pub. Date: Oct. 9, 2014

(65) Prior Publication Data
US 2016/0061920 A1 Mar. 3, 2016

Related U.S. Application Data

(60) Provisional application No. 61/807,996, filed on Apr. 3, 2013.

(51) Int. Cl.
*G06K 9/00* (2006.01)
*G01R 33/56* (2006.01)
(Continued)

(52) U.S. Cl.
CPC ........ *G01R 33/5602* (2013.01); *A61B 5/0044* (2013.01); *A61B 5/055* (2013.01);
(Continued)

(58) Field of Classification Search
CPC . A61B 5/055; A61B 2576/023; A61B 5/0044; G01R 33/56341; G01R 33/5602;
(Continued)

(56) References Cited

U.S. PATENT DOCUMENTS

| 2002/0042569 A1* | 4/2002 | Wedeen | A61B 5/055 |
| | | | 600/411 |
| 2011/0091118 A1* | 4/2011 | Ahn | G06T 9/001 |
| | | | 382/232 |

OTHER PUBLICATIONS

Hales, P. et al., Histo-anatomical structure of the living isolated rat heart in two contraction states assessed by diffusion tensor MRI; Progress in Biophysics and Molecular Biology, vol. I 10, Issue 2-3, Aug. 7, 2012, pp. 319-330 [online], Retreived from the internet: <URL:http://www.sciencedirect.com/science/article/pii/S0079610712000673>.*

(Continued)

*Primary Examiner* — Gregory F Cunningham
(74) *Attorney, Agent, or Firm* — Quarles & Brady LLP

(57) ABSTRACT

Systems and methods are provided for mapping myocardial tissue architecture based on diffusion tensor imaging (DTI). A set of eigenvectors is derived from diffusion tensor data, where each eigenvector describes the diffusion of spins along one of the Cartesian directions. A radial coordinate axis and a circumferential plane are determined based on anatomical information of the subject, such as from an image depicting the epicardial surface of the subject's heart, A longitudinal coordinate axis and a circumferential coordinate axis are determined based on the radial coordinate axis and circumferential plane, A fiber architecture matrix (FAM) is then computed for locations in the subject's heart based on projecting the set of eigenvectors onto a local coordinate system defined by the circumferential, radial, and longitudinal axes, Maps that represent myocardial tissue architecture can then be generated using the FAM for locations within the subject's heart.

14 Claims, 8 Drawing Sheets

(51) Int. Cl.
  *A61B 5/055* (2006.01)
  *G01R 33/563* (2006.01)
  *A61B 5/00* (2006.01)
  *G06T 7/00* (2017.01)
  *G06T 11/00* (2006.01)
  *G06T 7/11* (2017.01)

(52) U.S. Cl.
  CPC ...... *G01R 33/56341* (2013.01); *G06T 7/0012* (2013.01); *G06T 7/11* (2017.01); *G06T 11/003* (2013.01); *A61B 2576/023* (2013.01); *G06T 2207/10088* (2013.01); *G06T 2207/30048* (2013.01)

(58) Field of Classification Search
  CPC ......... G06T 2207/10088; G06T 11/003; G06T 7/0081; G06T 7/0012; G06T 2207/30048
  USPC ........................................................ 382/131
  See application file for complete search history.

(56) References Cited

OTHER PUBLICATIONS

International Search Report and Written Opinion as mailed on Aug. 18, 2014 for International Application No. PCT/US2014/032766.

Hales, P. et al., Histo-anatomical structure of the living isolated rat heart in two contraction states assessed by diffusion tensor MRI; Progress in Biophysics and Molecular Biology, vol. 110, Issue 2-3, Aug. 7, 2012, pp. 319-330 [online], Retreived from the Internet: <URL: http://www.sciencedirect.com/science/article/pii/S0079610712000673>.

Chen. J. et al., Remodeling of cardiac fiber structure after infarction in rats quantified with diffusion tensor MRI, Am J Physiol Heart Circ Physiol 285, May 22, 2003: pp. H946-H954 [online]. Retrieved from internet: <URL:http//www.sciencedirect.com/science/article/pii/S0079610712000673>.

\* cited by examiner

MAPPING CARDIAC TISSUE ARCHITECTURE SYSTEMS AND METHODS

CROSS-REFERENCE TO RELATED APPLICATIONS

This application represents the U.S. National Stage of International Application No. PCT/US2014/032766, filed Apr. 3, 2014 which claims the benefit of U.S. Provisional Patent Application Ser. No. 61/807,996, filed Apr. 3, 2013, and entitled "Fiber Architecture Matrix."

STATEMENT REGARDING FEDERALLY SPONSORED RESEARCH

This invention was made with government support under HL093038 and RR14075 awarded by the National Institutes of Health. The government has certain rights in the invention.

BACKGROUND

The present disclosure relates generally to systems and methods for magnetic resonance imaging ("MRI") and, in particular, to systems and methods for mapping cardiac fiber architecture using diffusion-weighted imaging techniques, such as diffusion tensor imaging.

For diffusion MRI techniques, motion sensitizing magnetic field gradients are applied using diffusion weighted imaging ("DWI") pulse sequences so that the magnetic resonance images include contrast related to the diffusion of water or other fluid molecules. Since microscopic arrangements of tissues often constrain diffusion such that fluid mobility may not be the same in all directions, applying diffusion gradients in several selected directions during the MRI measurement cycle allows diffusion weighted images to be acquired, from which diffusion properties, or coefficients, may be obtained. In the brain, for example, water molecules diffuse more readily along directions of axonal fiber bundles as compared with directions partially or totally orthogonal to the fibers. Hence, the directionality and anisotropy of the apparent diffusion coefficients tend to correlate with the direction of the axonal fibers and fiber bundles. Similarly, in the heart, water diffuses preferentially along myofibers, and so diffusion-encoded imaging techniques allow fiber orientation to be resolved. Hence, application of various processing methods to the diffusion data, allows fibers or fiber bundles to be tracked or segmented, providing indications of normal, injured or diseased tissue construction.

Specifically, in the case of diffusion tensor imaging ("DTI"), three-dimensional distributions of fluid mobility may be represented via tensor field formalism. In order to obtain the apparent diffusion tensor coefficients describing the diffusion tensor, it is generally necessary to acquire at least six DWI images using motion-sensitizing gradients directed in six different directions. Indeed, it may be desirable to acquire more than six directions, but the acquisition of additional DWI images may extend the total scan time. As is known in the art, a diffusion tensor for each voxel provides a reference frame, or eigensystem, that includes orthogonal axes termed eigenvectors, $\hat{e}_i$, whereby eigenvalues, $\lambda_i$, along the eigenvectors correspond to the degree of diffusivity along each of the major axes of the diffusion tensor. Typically, the orientation of the tensor is commonly taken to be parallel to the principal eigenvector, $\hat{e}_1$, describing the direction of largest diffusion, or the eigenvector associated with the largest eigenvalue, $\lambda_1$. For anisotropic fluid diffusion, as observed along tissue fibers or fiber bundles, the principal eigenvector is generally assumed to be collinear with the dominant fiber or fiber bundle orientation.

In particular, heart wall myofibers have been shown to wind as helices around the ventricle chambers, having been resolved by way of histological investigations using sectioned samples, as well as using non-invasive imaging, such as DTI techniques. Presenting additional complication, in vivo data has shown that myofiber architecture is dynamic, as in the case when the left ventricle ("LV") contracts and relaxes. Microstructural changes in tissues, like the myocardium, are commonly quantified by measuring invariants of the tensors, such as mean diffusivity ("MD"), fractional anisotropy ("FA"), or mode for each location, or voxel, in a region of interest. These invariants provide a basis for comparing tensor components between different tissues or regions. Specifically, the MD describes an average diffusivity, while the FA measures the magnitude of the anisotropic component of the tensor, and the mode describes the type of anisotropy, such as planar anisotropic, orthotropic, or linear anisotropic.

These indices have been widely used in ex vivo cardiac DTI studies of both healthy and diseased myocardium, and have been used in humans in vivo to characterize the microstructural integrity of the myocardium after infarction. Most architecture-related information derived from the DTI data has relied solely upon the diffusion along the principal eigenvector. For example, the helix angle ("HA") metric relies upon the orientation, or inclination, of the principal eigenvector, while a more recent approach quantifies a propagation angle (PA) that measures the angle between two adjacent principal eigenvectors relative to a given myofiber. However, the ability of these metrics to fully characterize structural dynamics during heart activity is limited, and their reproducibility in the human heart in vivo is unknown.

Therefore, given the above, there is a need for systems and methods directed to improved myocardial tissue architecture mapping.

SUMMARY OF THE INVENTION

The present invention overcomes the aforementioned drawbacks by providing systems and methods directed to mapping myocardial tissue architecture using diffusion-weighted imaging techniques, such as diffusion tensor imaging ("DTI"), and a local cardiac coordinate system to derive a fiber architecture matrix ("FAM") capable of fully characterizing local myofiber morphology.

It is an aspect of the present invention to provide a method for mapping myocardial tissue architecture using magnetic resonance imaging. DTI data acquired from a subject's heart using an MRI system is provided, from which a set of eigenvectors that describe diffusion along a set of Cartesian directions is determined. An image that depicts an epicardial surface of the subject's heart is also provided. A radial coordinate axis and a circumferential plane are determined using the image that depicts the epicardial surface of the subject's heart. A longitudinal coordinate axis based on the radial coordinate axis and circumferential plane is determined, as is a circumferential coordinate axis based on the radial coordinate axis and the longitudinal coordinate axis. A FAM is produced by projecting the set of eigenvectors onto radial, longitudinal, and circumferential planes in a local coordinate system defined by the determined radial, longitudinal, and circumferential coordinate axes. Using this FAM, a map that is representative of myocardial tissue architecture for locations within a region of interest in the subject's heart can be generated.

The foregoing and other advantages of the invention will appear from the following description.

DETAILED DESCRIPTION

Traditional diffusion tensor imaging ("DTI") studies of the heart generally rely on a global cardiac coordinate system that does not take local changes in cardiac morphology into account. The systems and methods described here, however, provide a solution to this problem by mapping myocardial tissue architecture based on projecting information derived from a diffusion tensor into a local, subject-specific cardiac coordinate system. More particularly, the systems and methods described here include computing a fiber architecture matrix ("FAM") based on projections of eigenvectors, such as those derived from a diffusion tensor, onto a local coordinate system that more accurately characterizes diffusion in the myocardial tissue.

The FAM serves as a function of the complete diffusion tensor eigensystem, and is designed to characterize myocardial tissue dynamics both in vivo and ex vivo. The relationship between the eigensystem and the local cardiac coordinate system, provided by the FAM, characterizes the structural dynamics of heart function, such as left ventricular contraction. The FAM encodes myocardial tissue architecture using the projections of all three diffusion tensor eigenvectors with respect to radial, circumferential, and longitudinal planes that fully represent a local cardiac coordinate system. This local cardiac coordinate system is determined for the particular subject being imaged and is based on information derived from anatomical images of the subject.

In particular, coefficients of the FAM, as shown in Eqn. (1) below, locally encode the angles between projections of eigenvectors $\hat{e}_1$, $\hat{e}_2$, and $\hat{e}_3$ with respect to circumferential ("C"), radial ("R") and longitudinal ("L") planes.

$$FAM = \begin{bmatrix} \langle \hat{L}, proj_{\hat{e}_1}C \rangle & \langle \hat{C}, proj_{\hat{e}_1}R \rangle & \langle \hat{R}, proj_{\hat{e}_1}L \rangle \\ \langle \hat{L}, proj_{\hat{e}_2}C \rangle & \langle \hat{C}, proj_{\hat{e}_2}R \rangle & \langle \hat{R}, proj_{\hat{e}_2}L \rangle \\ \langle \hat{L}, proj_{\hat{e}_3}C \rangle & \langle \hat{C}, proj_{\hat{e}_3}R \rangle & \langle \hat{R}, proj_{\hat{e}_3}L \rangle \end{bmatrix} = \begin{bmatrix} \hat{e}_1^C & \hat{e}_1^R & \hat{e}_1^L \\ \hat{e}_2^C & \hat{e}_2^R & \hat{e}_2^L \\ \hat{e}_3^C & \hat{e}_3^R & \hat{e}_3^L \end{bmatrix}; \quad (1)$$

where $\langle \ldots, \ldots \rangle$ is the inner product of two vectors, $\hat{L}$ is a unit vector along the longitudinal axis, $\hat{C}$ is a unit vector along the circumferential axis, $\hat{R}$ is a unit vector along the radial axis, and $proj_{\hat{e}_j}$ indicates the projection of an eigenvector (j=1, 2, 3) onto the circumferential, radial, or longitudinal plane, as indicated in Eqn. (1). Hence the FAM is representative of myocardial tissue architecture based on a local, or cardiac, coordinate system that is a function of cardiac morphology.

Figure 1:
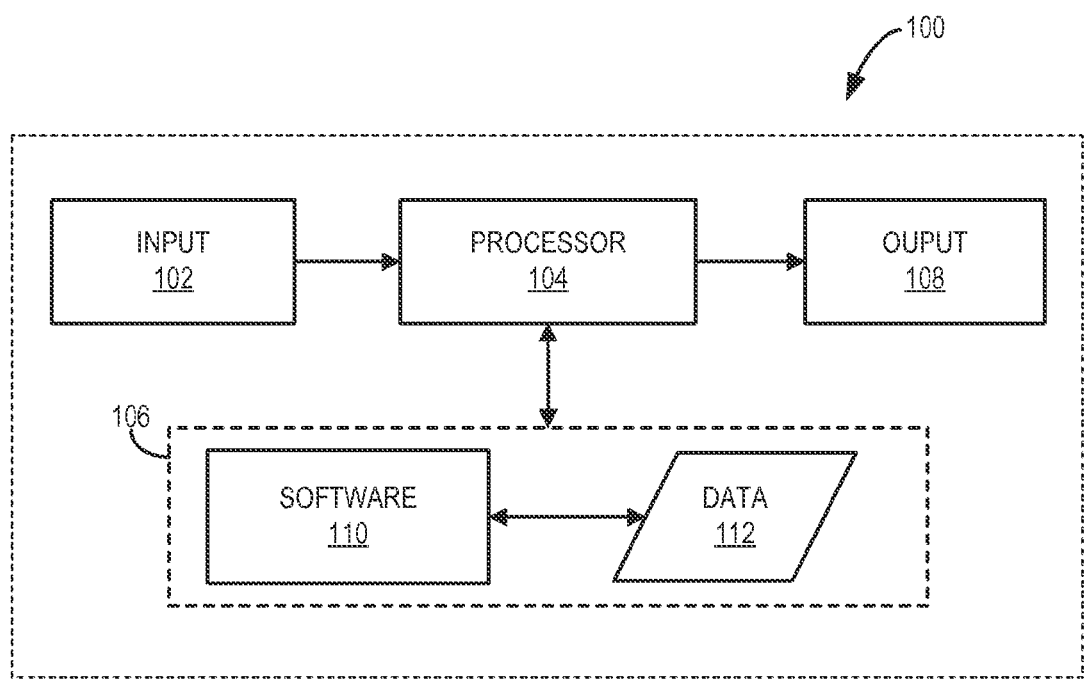
FIG. 1 is a block diagram of an example of a computer system that is configured for use as a fiber architecture mapping system, in accordance with some embodiments of the present invention.

Turning to FIG. 1, a block diagram of an example system 100 that can be used for producing cardiac fiber architecture mapping of a subject's heart is illustrated. The system 100 generally may include an input 102, at least one processor 104, a memory 106, an output 108, and any device for reading computer-readable media (not shown). The system 100 may be, for example, a workstation, a notebook computer, a personal digital assistant (PDA), a multimedia device, a network server, a mainframe or any other general-purpose or application-specific computing device, or a system in communication with or part of a magnetic resonance system ("MRI"), as will be described. The system 100 may operate autonomously or semi-autonomously, or may read executable software instructions from a computer-readable medium (such as a hard drive, a CD-ROM, flash memory and the like), or may receive instructions from a user, or any another source logically connected to a computer or device, such as another networked computer or server, via the input 102.

The input 102 may take any shape or form, as desired, for operation of the system 100, including the ability for selecting, entering or otherwise specifying parameters consistent with operating the system 100. In some aspects, the input 102 may be designed to accept DTI data describing diffusion along a set of Cartesian directions or axes for locations within, for example, a subject's heart. The input 102 may also be configured to receive other imaging data, such as imaging indicative of cardiac anatomy. Such data may be pre-processed, filtered and corrected using any suitable systems and methods.

Among the processing tasks for operating the system 100, the at least one processor 104 may also be configured to receive DTI data, wherein the received DTI data may be pre-processed, and/or may undergo any number of further processing steps using the at least one processor 104. In some aspects, the at least one processor 104 may be capable of performing computations using signals derived from DTI data. For example, the at least one processor 104 may be capable, using the DTI data, of determining a set of eigenvectors and eigenvalues describing diffusion along Cartesian directions for any number of locations, or voxels, within a region of interest, such as a subjects' heart. Specifically, the at least one processor 104 may be designed to implement a nonlinear least-squares curve-fitting technique using signal intensity attenuation to determine diffusion tensor components and be capable of diagonalizing such tensors to obtain the eigenvalues.

The at least one processor 104 may also be configured to create a local coordinate system for each location, or voxel, within a region the interest by determining a radial, circumferential and longitudinal axis for each location. In particular, the at least one processor 104 may be configured to compute a Euclidean distance map with respect to any target locations or points of reference, such as an epicardial surface, using, for example, a planar wave propagation technique, and compute a gradient vector field using the Euclidean distance map. In some aspects, target locations or points of reference may be generated autonomously by the at least one processor 104 using anatomical data, or may be selected, segmented by, or in combination with a user input. Using the radial, circumferential and longitudinal coordinate axes, the at least one processor 104 may further be configured to produce local FAMs for each location, or voxel, within the region of interest by projecting the set of eigenvectors onto coordinate systems defined by the radial, circumferential and longitudinal coordinate axes. In some aspects, the at least one processor 104 may be designed to perform computations related to fiber tractography, including numerical integration methods, such as 4th order Runge-Kutta. In addition, the at least one processor 104 may be configured to process or perform computations using time-series data. For example, such computations may be representative of, or specific to time points or periods of a cardiac cycle, such as diastole or systole periods. Furthermore, the at least one processor 104 may also be configured to create two or three dimensional maps, tractography maps, and so forth indicative of fiber architecture and fiber architecture dynamics for subsequent use, analysis or display via the output 112.

The memory 106 may contain software 108 and data 110, and may be configured for storage and retrieval of processed information and data to be processed by the processor 104. In some aspects, the software 110 may contain instructions directed to producing local FAMs for locations, or voxels, within a region of interest, as mentioned. The data 112 may take include any data necessary for operating the system 100, and may include any raw or processed information in relation to anatomical data, diffusion data, and so forth. In addition, the output 112 may take any shape or form, as desired, and may be configured for displaying, in addition to other desired information, any information in relation to fiber architecture and fiber architecture dynamics. For example, output 112 may be configured to display two or three dimensional maps, tractography maps, and so forth indicative of fiber architecture and fiber architecture dynamics.

Figure 2:
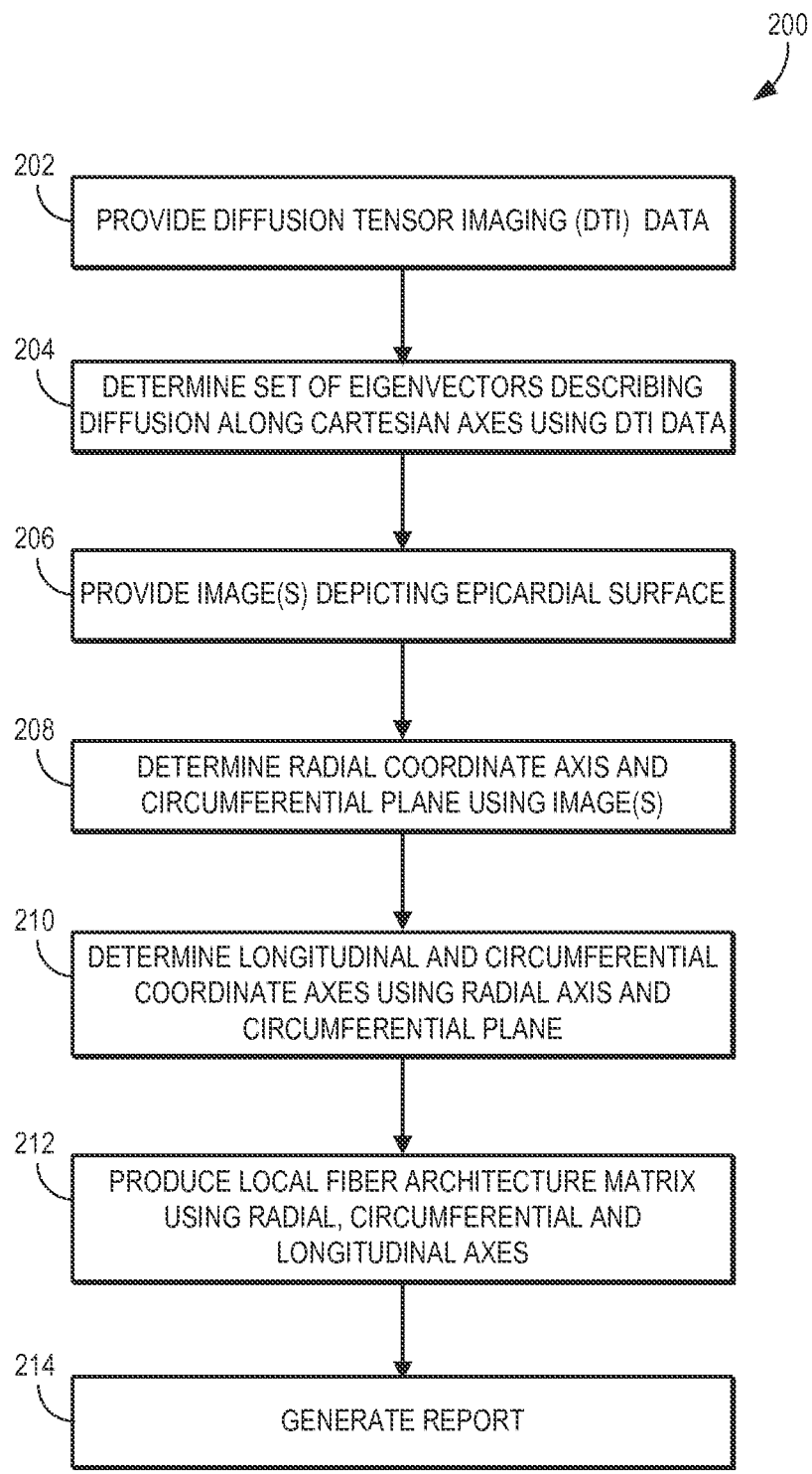
FIG. 2 is a flowchart setting forth steps of an example fiber architecture mapping method in accordance with some embodiments of the present invention.

Turning to FIG. 2, an example process 200 is illustrated setting forth steps of a method in accordance with some embodiments of the present invention. The process 200 may begin at process block 202, wherein DTI data acquired from a subject's heart is provided. In some aspects, DTI data may include time-series signals representative of, or specific to, time points or periods of a cardiac cycle, such as diastole or systole periods. As an example, the DTI data may be provided by retrieving the data from a data storage. As another example, the DTI data can be provided by acquiring it from the subject using an MRI system. For instance, as one non-limiting example, DTI data can be acquired by performing diffusion tensor imaging using any suitable, known pulse sequence, such as one with the following parameters: 6 diffusion-encoding directions, b=350 s/mm$^2$, TR=1100 ms, TE=23 ms. Then at process block 204, a set of eigenvectors indicative of diffusion along a set of Cartesian directions, or axes, may be determined using the DTI data for any locations, or voxels, within a region of interest. For instance, a diffusion tensor is computed at each voxel location based on the DTI data and from the diffusion tensor the three eigenvectors, $(\hat{e}_1, \hat{e}_2, \hat{e}_3)$, that describe diffusion along the Cartesian axes can be derived.

A local cardiac coordinate system defined by radial, circumferential, and longitudinal axes can then be created at each voxel based on anatomical information for the particular subject being imaged. As an example, the local cardiac coordinate system is defined within the subject's myocardium, assuming the geometry of the left ventricle. At process block 206 at least one image depicting the subject's heart may be provided. By way of example, the image preferably depicts the epicardial surface of the subject's heart.

Figure 3A:
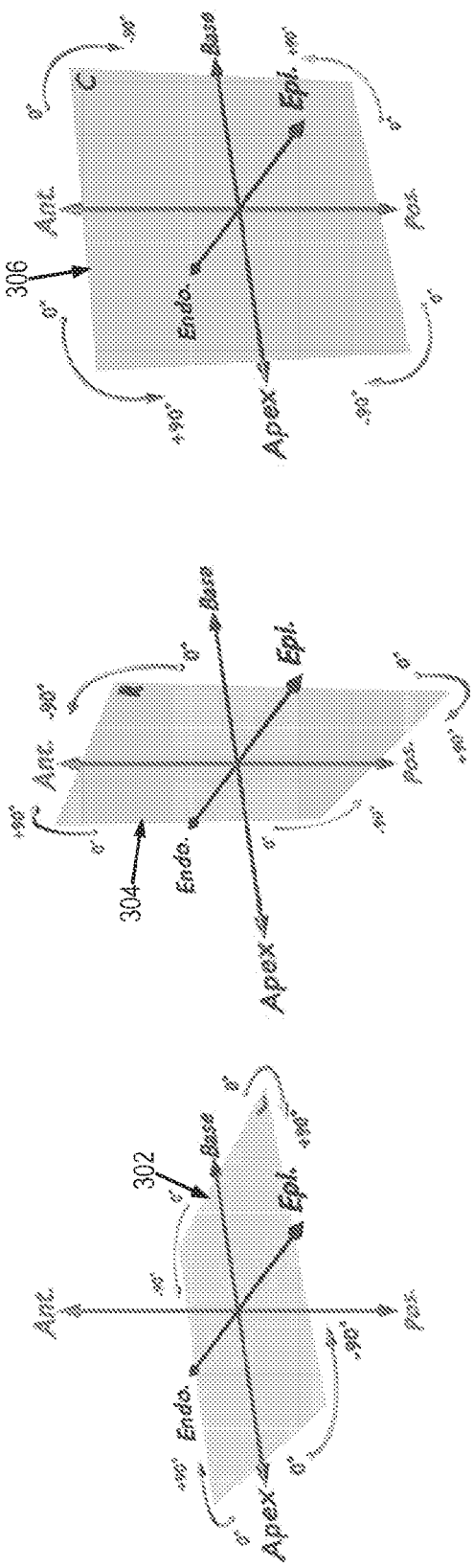
FIG. 3A is a schematic illustrating longitudinal, radial and circumferential cardiac planes in a locally-defined cardiac coordinate system.

An example of a local cardiac coordinate system is illustrated in FIG. 3A, which illustrates a longitudinal plane 302, a radial plane 304, and a circumferential plane 306. In this example, the longitudinal plane is perpendicular to an axis that extends along the anterior-posterior direction of the subject; the radial plane is perpendicular to an axis that extends along the apex-base direction of the subject's heart; and the circumferential plane is perpendicular to an axis that extends along the endocardial-epicardial direction of the subject's heart.

The provided image of the subject's heart may then be used at process block 208 to determine a radial coordinate axis and a circumferential plane for each location, or voxel, within the region of interest. In particular, this may be accomplished by first producing a Euclidean distance map from regions or points of reference, such as the epicardial surface. In some embodiments, the Euclidean distance map may be computed using a planar wave propagation technique. The distance map may then be used to compute or otherwise derive a gradient vector field, from which radial coordinate axes and circumferential planes are determined. For instance, a gradient vector field resulting from the planar wave propagation determines the radial axis and circumferential plane at each imaged location of the subject's heart. At process block 210, the longitudinal coordinate axis may then be determined from a projection of, for example, an apex-base direction onto the determined circumferential plane (FIG. 3A), and the circumferential coordinate axis may be computed via a cross product between the radial and longitudinal coordinate axes.

Figure 3B:
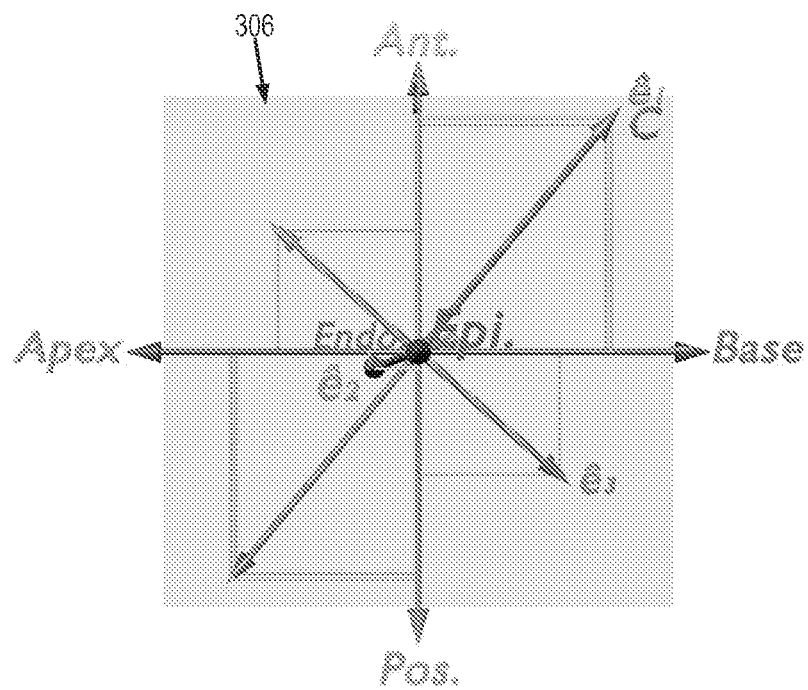
FIG. 3B is a schematic illustrating projection of eigenvectors derived from a diffusion tensor onto a circumferential plane in a locally-defined cardiac coordinate system.

At process block 212 a local fiber architecture matrix ("FAM"), which is a second order matrix, is determined by projecting the set of eigenvectors derived from the DTI data onto the coordinate system defined by the circumferential, radial, and longitudinal axes. An example of this process is graphically illustrated in FIG. 3B, which shows the projections of the eigenvectors, $(\hat{e}_1, \hat{e}_2, \hat{e}_3)$, onto the circumferential plane 306, thereby resulting in the $\hat{e}_1^C$, $\hat{e}_2^C$, and $\hat{e}_3^C$ coefficients of the FAM. From the coefficients in the FAM, the angles between projections of the eigenvectors, $(\hat{e}_1, \hat{e}_2, \hat{e}_3)$, and the circumferential, radial, and longitudinal axes can be computed using vector analysis techniques. As an example, the angle, $\theta$, between the longitudinal axis, $\hat{L}$, and the projection of the principal eigenvector, $\hat{e}_1$, onto the circumferential plane, $\text{proj}_{\hat{e}_1} C$, can be determined as follows, $$\theta = \cos^{-1}\left(\frac{\langle \hat{L},\ \text{proj}_{\hat{e}_1} C \rangle}{\|\hat{L}\| \|\text{proj}_{\hat{e}_1} C\|}\right) = \cos^{-1}\left(\frac{\langle \hat{L},\ \text{proj}_{\hat{e}_1} C \rangle}{\|\text{proj}_{\hat{e}_1} C\|}\right). \quad (2)$$

Hence the FAM is representative of cardiac fiber architecture based on a local, or cardiac, coordinate system that is a function of cardiac morphology. Then at process block 214 a report may be generated, which could take any desired shape or form. For example, the report may include two or three dimensional maps based on coefficients of the FAM, tractography maps built using the FAM, and so on. These generated reports thus generally provide indications of myocardial tissue fiber architecture and myocardial tissue fiber architecture dynamics. As mentioned above, the FAM can be computed for the same locations at different time points in the cardiac cycle. Accordingly, the FAM can provide dynamic information about the changes in myocardial tissue architecture during different cardiac phases, such as end systole and end diastole.

Figure 4A:
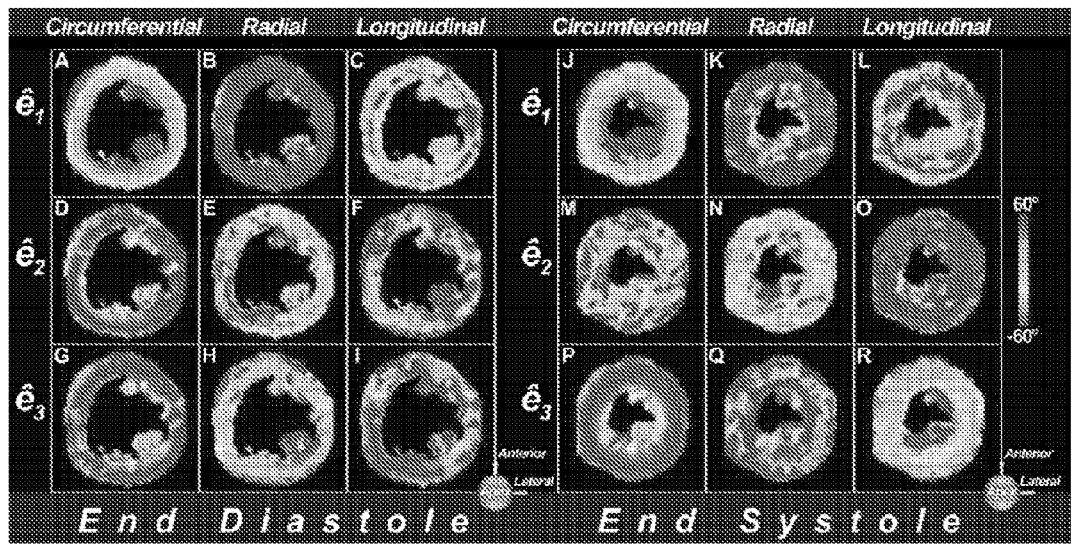
FIG. 4A is an example of two-dimensional maps generated based on the fiber architecture matrix coefficients.
Figure 4B:
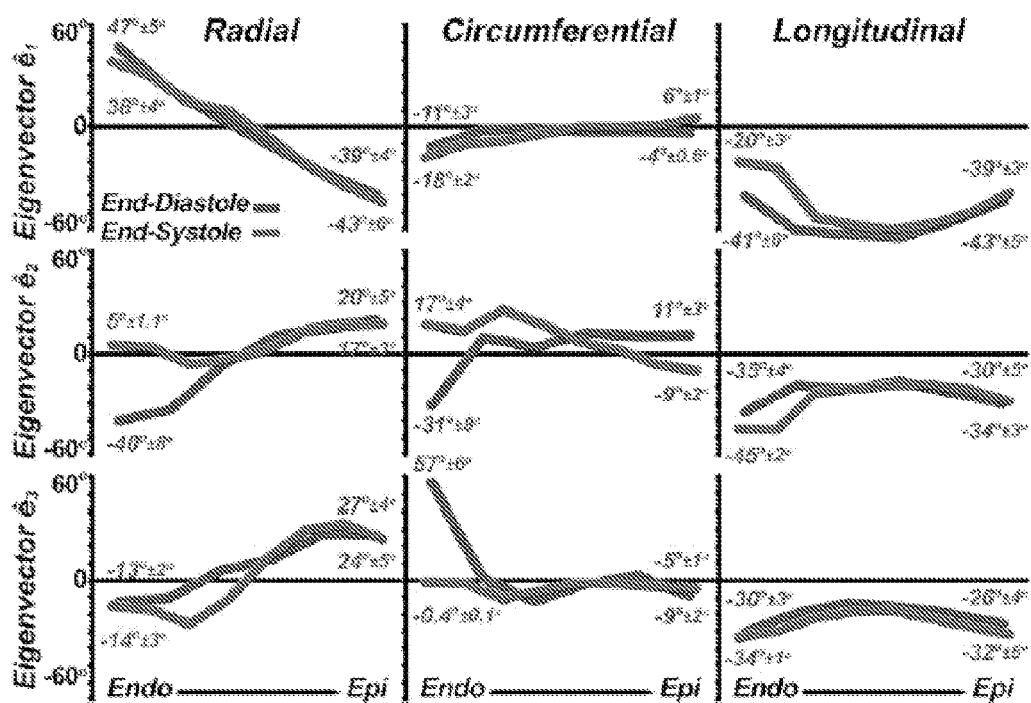
FIG. 4B illustrates a series of plots comparing projection angles for eigenvectors with respect to planes defined by radial, circumferential, and longitudinal coordinate axes for end-diastole and end-systole periods of the cardiac cycle.

As an example, FIG. 4A, depicts FAM coefficient maps of a short-axis slice in a normal human heart for the end-diastole and end-systole periods of the heart cycle. Note that in addition to coefficient $\langle \hat{C}, \text{proj}_{\hat{e}_1} R \rangle$, also known as the helix angle ("HA"), all the projection angles contribute to the complete description of myocardial architecture and dynamics. FIG. 4B shows the distribution of the FAM coefficients for the hearts imaged in vivo at end-diastole and end-systole. Angular variations between systole and diastole were seen for all coefficients, although the most significant changes were seen in $\langle \hat{C}, \text{proj}_{\hat{e}_2} R \rangle$, $\langle \hat{L}, \text{proj}_{\hat{e}_2} C \rangle$, and $\langle \hat{L}, \text{proj}_{\hat{e}_3} C \rangle$ in the sub-endocardium. These changes depict myofiber reconfiguration in systole due to myocyte thickening, sheet sliding, and sheet shearing.

Figures 5A, 5B, 5C:
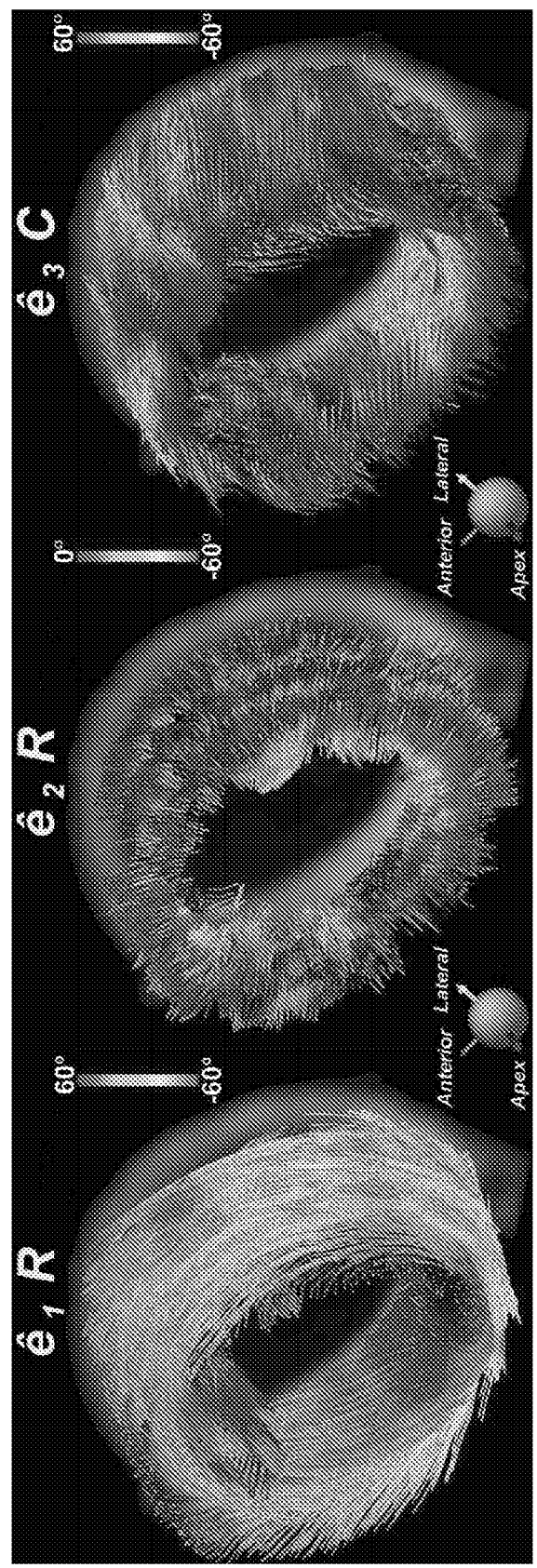
FIGS. 5A-5C illustrate examples of three-dimensional fiber tracts for eigenvectors projected onto radial and circumferential planes.
Figure 6:
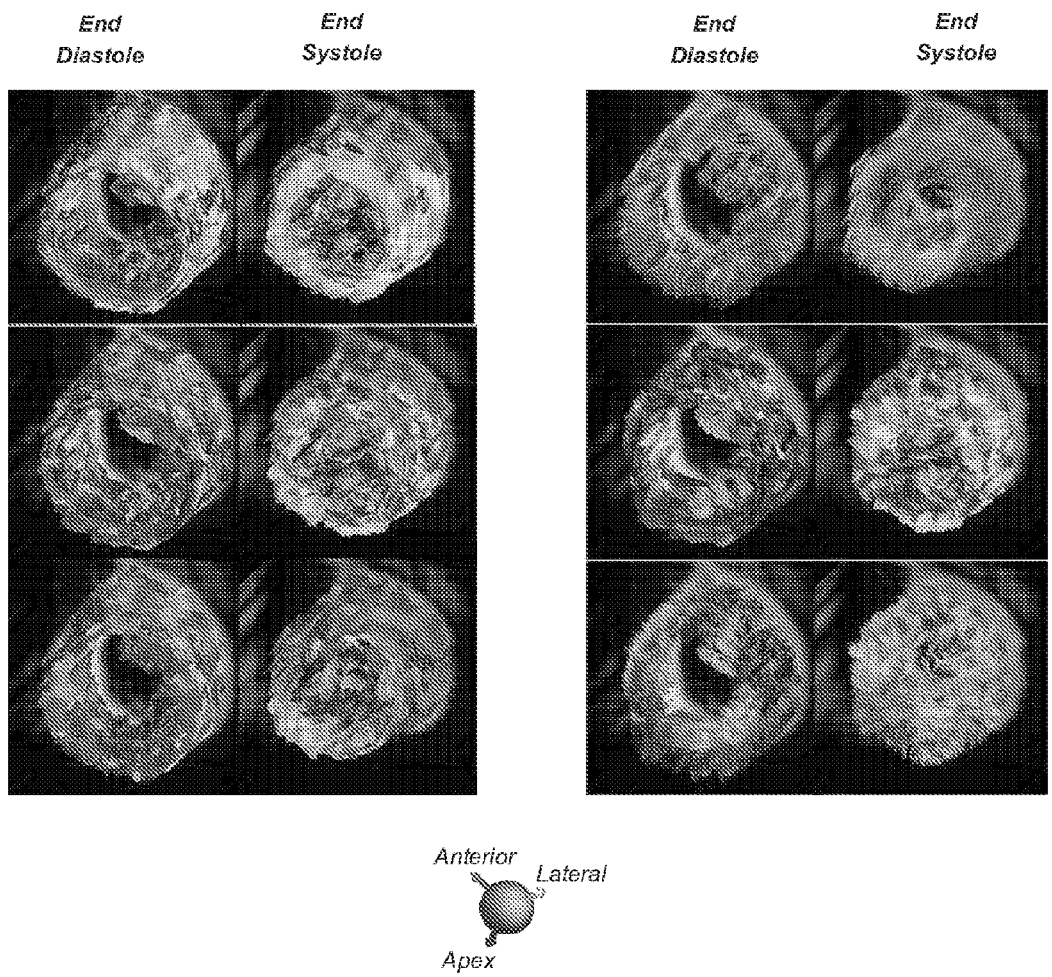
FIG. 6 is a graphical illustration comparing three-dimensional fiber tracts for end-diastole and end-systole periods of the cardiac cycle.

In addition to the two-dimensional maps shown in FIG. 4A, fiber tracts can be constructed by integrating $\hat{e}_1$, $\hat{e}_2$, and $\hat{e}_3$ into connected tracts, or streamlines. As an example, these tracts can be generated using a 4th order Runge-Kutta method. The tracts are then color coded based on their projection onto any of the radial, longitudinal, or circumferential cardiac planes. For example, in FIG. 5A, $\hat{e}_1$-based tracts coded by their projection onto the radial plane are shown. These tracts represent myofiber tracts coded by the helix, or spiral, angle they move through the left ventricle. Sheet tracts coded by the projection of $\hat{e}_2$ onto the radial plane are shown in FIG. 5B. The radial orientation of the myofiber sheets and the change in the sheet angle from the epicardium to the endocardium can be clearly seen. In addition, FIG. 5C shows longitudinal tracts of $\hat{e}_3^C$, illustrating that the tertiary eigenvector in the left ventricle is largely oriented from base to apex. Furthermore, cardiac dynamics can also be examined using the FAM, as shown in FIG. 6. Specifically, myofiber reorganization, which is predominantly in sheet structure, can be imaged during systole as the heart contracts.

Generally, diagonalization of the diffusion tensor produces three eigenvectors that indicate diffusion along the three principal Cartesian axes. It has been shown here that a second order fiber architecture matrix ("FAM") can be computed based on the projections of each of these eigenvectors onto three, locally-defined cardiac planes. Independent and complimentary information is contained in each coefficient in the FAM, which can be used to create two-dimensional maps or three-dimensional tracts of myocardial tissue architecture. While helical angle can provide information about angular differences in the orientation of myofibers, as observed across the left ventricular wall, the helical angle alone does not provide sufficient information to fully characterize the myocardial tissue architecture. The information provided in the FAM described here, however, is computed based on the entire eigensystem of the diffusion tensor and thus is capable of fully characterizing cardiac dynamics, such as exhibited during left ventricular contraction.

As such, the approach of the present invention provides a foundation for combining information from diffusion tensor and strain tensor datasets to better understand cardiac mechanics. In this manner, the characterization of myofiber architecture using the FAM, in cases of the normal and infarcted heart, may demonstrate significant promise for detection, evaluation, or treatment of disease.

Figure 7:
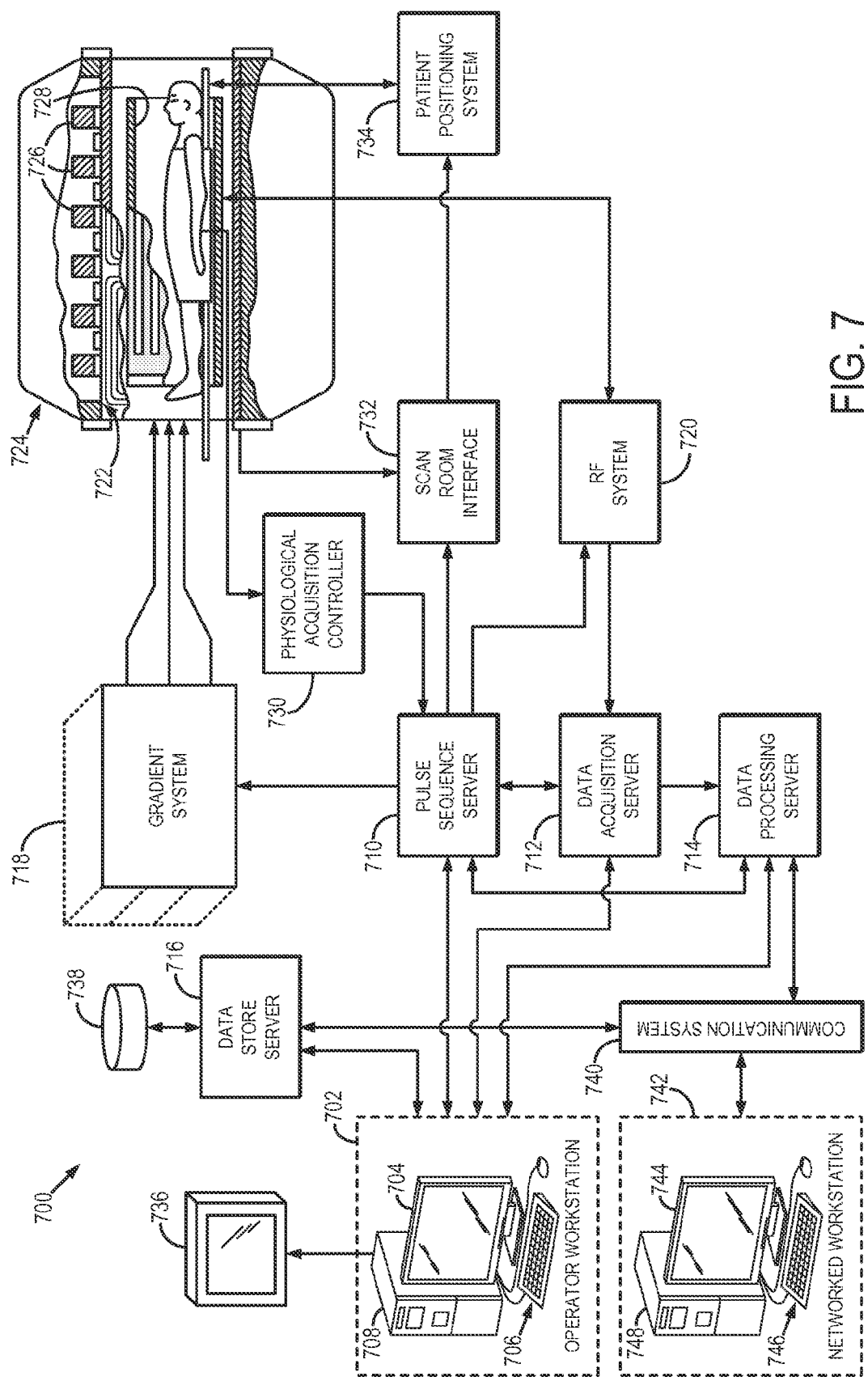
FIG. 7 is a block diagram of an example of a magnetic resonance imaging ("MRI") system.

Referring particularly now to FIG. 7, an example of a magnetic resonance imaging ("MRI") system 700 is illustrated. The MRI system 700 includes an operator workstation 702, which will typically include a display 704; one or more input devices 706, such as a keyboard and mouse; and a processor 708. The processor 708 may include a commercially available programmable machine running a commercially available operating system. The operator workstation 702 provides the operator interface that enables scan prescriptions to be entered into the MRI system 700. In general, the operator workstation 702 may be coupled to four servers: a pulse sequence server 710; a data acquisition server 712; a data processing server 714; and a data store server 716. The operator workstation 702 and each server 710, 712, 714, and 716 are connected to communicate with each other. For example, the servers 710, 712, 714, and 716 may be connected via a communication system 740, which may include any suitable network connection, whether wired, wireless, or a combination of both. As an example, the communication system 740 may include both proprietary or dedicated networks, as well as open networks, such as the internet.

The pulse sequence server 710 functions in response to instructions downloaded from the operator workstation 702 to operate a gradient system 718 and a radiofrequency ("RF") system 720. Gradient waveforms necessary to perform the prescribed scan are produced and applied to the gradient system 718, which excites gradient coils in an assembly 722 to produce the magnetic field gradients $G_x$, $G_y$, and $G_z$ used for position encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil (not shown in FIG. 7), in order to perform the prescribed magnetic resonance pulse sequence. Responsive magnetic resonance signals detected by the RF coil 728, or a separate local coil (not shown in FIG. 7), are received by the RF system 720, where they are amplified, demodulated, filtered, and digitized under direction of commands produced by the pulse sequence server 710. The RF system 720 includes an RF transmitter for producing a wide variety of RF pulses used in MRI pulse sequences. The RF transmitter is responsive to the scan prescription and direction from the pulse sequence server 710 to produce RF pulses of the desired frequency, phase, and pulse amplitude waveform. The generated RF pulses may be applied to the whole-body RF coil 728 or to one or more local coils or coil arrays (not shown in FIG. 7).

The RF system 720 also includes one or more RF receiver channels. Each RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I^2+Q^2} \qquad (3);$$

and the phase of the received magnetic resonance signal may also be determined according to the following relationship:

$$\varphi = \tan^{-1}\left(\frac{Q}{I}\right). \quad (4)$$

The pulse sequence server 710 also optionally receives patient data from a physiological acquisition controller 730. By way of example, the physiological acquisition controller 730 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 710 to synchronize, or "gate," the performance of the scan with the subject's heart beat or respiration.

The pulse sequence server 710 also connects to a scan room interface circuit 732 that receives signals from various sensors associated with the condition of the patient and the magnet system. It is also through the scan room interface circuit 732 that a patient positioning system 734 receives commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, such that no data is lost by data overrun. In some scans, the data acquisition server 712 does little more than pass the acquired magnetic resonance data to the data processor server 714. However, in scans that require information derived from acquired magnetic resonance data to control the further performance of the scan, the data acquisition server 712 is programmed to produce such information and convey it to the pulse sequence server 710. For example, during prescans, magnetic resonance data is acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also be employed to process magnetic resonance signals used to detect the arrival of a contrast agent in a magnetic resonance angiography ("MRA") scan. By way of example, the data acquisition server 712 acquires magnetic resonance data and processes it in real-time to produce information that is used to control the scan.

The data processing server 714 receives magnetic resonance data from the data acquisition server 712 and processes it in accordance with instructions downloaded from the operator workstation 702. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 714 are conveyed back to the operator workstation 702 where they are stored. Real-time images are stored in a data base memory cache (not shown in FIG. 7), from which they may be output to operator display 712 or a display 736 that is located near the magnet assembly 724 for use by attending physicians. Batch mode images or selected real time images are stored in a host database on disc storage 738. When such images have been reconstructed and transferred to storage, the data processing server 714 notifies the data store server 716 on the operator workstation 702. The operator workstation 702 may be used by an operator to archive the images, produce films, or send the images via a network to other facilities.

The MRI system 700 may also include one or more networked workstations 742. By way of example, a networked workstation 742 may include a display 744; one or more input devices 746, such as a keyboard and mouse; and a processor 748. The networked workstation 742 may be located within the same facility as the operator workstation 702, or in a different facility, such as a different healthcare institution or clinic.

The networked workstation 742, whether within the same facility or in a different facility as the operator workstation 702, may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may exchanged between the data processing server 714 or the data store server 716 and the networked workstations 742, such that the data or images may be remotely processed by a networked workstation 742. This data may be exchanged in any suitable format, such as in accordance with the transmission control protocol ("TCP"), the internet protocol ("IP"), or other known or suitable protocols.

Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A method for mapping myocardial tissue architecture using magnetic resonance imaging, the steps of the method comprising:
    a) providing diffusion tensor imaging (DTI) data acquired from a subject's heart using an MRI system;
    b) determining from the DTI data, a set of eigenvectors that describe diffusion along a set of Cartesian directions;
    c) providing an image that depicts an epicardial surface of the subject's heart;
    d) determining a radial coordinate axis and a circumferential plane using the image that depicts the epicardial surface of the subject's heart;
    e) determining a longitudinal coordinate axis based on the radial coordinate axis and circumferential plane;
    f) determining a circumferential coordinate axis based on the radial coordinate axis and the longitudinal coordinate axis;
    g) producing a fiber architecture matrix (FAM) by projecting the set of eigenvectors onto radial, longitudinal, and circumferential planes in a local coordinate system defined by the determined radial, longitudinal, and circumferential coordinate axes; and h) generating a map representative of myocardial tissue architecture for locations within a region of interest in the subject's heart using the FAM.

2. The method of claim 1, wherein determining the radial coordinate axis in step d) includes producing a Euclidean distance map from the epicardial surface using a planar wave propagation technique and determining the radial coordinate axis based on the Euclidean distance map.

3. The method of claim 2, wherein determining the radial coordinate axis based on the Euclidean distance map includes computing a gradient vector field from the Euclidean distance map and determining the radial coordinate axis based on the gradient vector field.

4. The method of claim 1, wherein determining the circumferential plane in step d) includes determining the circumferential plane as a plane perpendicular to the determined radial coordinate axis.

5. The method of claim 1, wherein determining the longitudinal coordinate axis in step e) includes determining the longitudinal coordinate axis from a projection of an apex-base direction onto the determined circumferential plane.

6. The method of claim 1, wherein determining the circumferential coordinate axis in step f) includes computing a cross product between the determined radial coordinate axis and the determined longitudinal coordinate axis.

7. The method of claim 1, wherein producing the FAM in step g) includes computing inner products between the radial, longitudinal, and circumferential coordinate axes and the projections of the eigenvectors onto the radial, longitudinal, and circumferential planes.

8. The method of claim 7, wherein the FAM is produced in step g) by computing, $$FAM = \begin{bmatrix} \langle \hat{L}, proj_{\hat{e}_1}C \rangle & \langle \hat{C}, proj_{\hat{e}_1}R \rangle & \langle \hat{R}, proj_{\hat{e}_1}L \rangle \\ \langle \hat{L}, proj_{\hat{e}_2}C \rangle & \langle \hat{C}, proj_{\hat{e}_2}R \rangle & \langle \hat{R}, proj_{\hat{e}_2}L \rangle \\ \langle \hat{L}, proj_{\hat{e}_3}C \rangle & \langle \hat{C}, proj_{\hat{e}_3}R \rangle & \langle \hat{R}, proj_{\hat{e}_3}L \rangle \end{bmatrix};$$

wherein $\hat{R}$ is a unit vector along the radial coordinate axis; $\hat{L}$ is a unit vector along the longitudinal axis; $\hat{C}$ is a unit vector along the circumferential coordinate axis; $proj_{\hat{e}_j}R$ is a projection of a $j^{th}$ eigenvector onto the radial plane, R; $proj_{\hat{e}_j}L$ is a projection of a $j^{th}$ eigenvector onto the longitudinal plane, L; $proj_{\hat{e}_j}C$ is a projection of a $j^{th}$ eigenvector onto the circumferential plane, C; and $j=1, 2, 3$ is an index defining a principal eigenvector, $\hat{e}_1$, a secondary eigenvector $\hat{e}_2$, and a tertiary eigenvector, $\hat{e}_3$.

9. The method of claim 1, wherein step h) includes generating a map having pixels defined by a coefficient of the FAM.

10. The method of claim 1, wherein step h) includes generating a tractographic map based on information derived from the FAM.

11. The method of claim 10, wherein the information derived from the FAM includes an angle between one of the radial, longitudinal, and circumferential axes and a projection of one of the eigenvectors onto one of the radial, longitudinal, and circumferential planes.

12. The method of claim 1, wherein:
the DTI data provided in step a) comprises first DTI data acquired during a first cardiac phase and second DTI data acquired during a second cardiac phase;
step b) includes determining a first set of eigenvector from the first DTI data and a second set of eigenvectors from the second set of DTI data; and
step g) includes producing a first FAM based on the first set of eigenvectors and a second FAM based on the second set of eigenvectors.

13. The method of claim 12, further comprising generating a report that compares the first FAM with the second FAM, thereby indicating a change in myocardial tissue architecture from the first cardiac phase to the second cardiac phase.

14. The method of claim 12, wherein the first cardiac phase is end systole and the second cardiac phase is end diastole.

* * * * *